United States Patent [19]
Weetall et al.

[11] Patent Number: 5,620,857
[45] Date of Patent: Apr. 15, 1997

[54] OPTICAL TRAP FOR DETECTION AND QUANTITATION OF SUBZEPTOMOLAR QUANTITIES OF ANALYTES

[75] Inventors: Howard H. Weetall, Rockville; Kristian P. Helmerson, Germantown; Roni B. Kishore, North Potomac, all of Md.

[73] Assignee: United States of America, as represented by the Secretary of Commerce, Washington, D.C.

[21] Appl. No.: 473,979

[22] Filed: Jun. 7, 1995

[51] Int. Cl.$^6$ .................................................. G01N 33/53
[52] U.S. Cl. .......................... 435/7.1; 436/518; 436/527; 436/543; 436/547; 356/364
[58] Field of Search .................................. 436/527, 518, 436/543, 547, 174; 435/6, 7.1, 174, 7.93; 356/364

[56] References Cited

U.S. PATENT DOCUMENTS

| | | |
|---|---|---|
| 4,893,886 | 1/1990 | Ashkin et al. |
| 4,999,284 | 3/1991 | Ward et al. |
| 5,079,169 | 1/1992 | Chu et al. |
| 5,100,627 | 3/1992 | Buican et al. |
| 5,173,260 | 12/1992 | Zander et al. |
| 5,185,269 | 2/1993 | Wells. |

OTHER PUBLICATIONS

Venton, D.L. et al. Biochim. Biophys. Acta, vol. 797, pp. 343–347. 1984.
Block, S.M. Nature, vol. 360, pp. 493–495. Dec. 3, 1992.
Kuo, S.C. and M.P. Sheetz. Science, vol. 260, pp. 232–234. Apr. 9, 1993.
Kuo, S.C. and D.A. Lauffenburger. Biophys. J., vol. 65, pp. 2191–2200. Nov. 1993.
Wolenski, J.S. et al. J. Cell Science, vol. 108, pt. 4, pp. 1489–1496. Apr. 1995.
Buti, M. et al. Eur. J. Clin. Chem. Clin. Biochem., vol. 29, pp. 731–735. Nov. 1991.

Primary Examiner—James C. Housel
Assistant Examiner—Rachel Freed
Attorney, Agent, or Firm—Watson Cole Stevens Davis, P.L.L.C.

[57] ABSTRACT

Tightly focused beams of laser light are used as "optical tweezers" to trap and manipulate polarizable objects such as microspheres of glass or latex with diameters on the order of 4.5 μm. When analytes are allowed to adhere to the microspheres, small quantities of these analytes can be manipulated, thus allowing their detection and quantitation even when amounts and concentrations of the analytes are extremely small. Illustrative examples include measuring the strength needed to break antibody-antigen bonds and the detection of DNA sequences.

10 Claims, 2 Drawing Sheets

OPTICAL TRAP FOR DETECTION AND QUANTITATION OF SUBZEPTOMOLAR QUANTITIES OF ANALYTES

FIELD OF THE INVENTION

This invention is directed to a method and device for the detection of sub-zeptomolar quantities of analytes, including nucleic acids, antigens (either soluble or as components of bacteria or viruses), antibodies, receptor molecules, lectins and other binding pairs (protein, carbohydrate, organic molecules, etc.), by optical trapping.

BACKGROUND OF THE INVENTION

Tightly focused beams of laser light can be used to trap and remotely manipulate polarizable objects. Originally proposed for the trapping of atoms, such devices are also capable of trapping macroscopic, polarizable objects such as latex and glass spheres in the micron size range as well as biological material such as viruses, bacteria, yeast and protozoa, ranging in size from 20 nm to 100 microns. The non-invasive trapping and manipulation of such object have led to the name "optical tweezers" for such devices. The basic principle behind optical tweezers is the gradient force of light which manifests itself when a transparent material with a refractive index greater than the surrounding medium is placed in a light intensity gradient. As light passes through the polarizable object, it induces fluctuating dipoles in the material. These dipoles interact with the electromagnetic field gradient, resulting in a force directed towards the brighter region of the light. Hence the object is pulled into the focus of the laser beam which is the local maximum of the light rigid. Typically, he focus of the laser beam is kept fixed (on the order of the wavelength) so the strength of the trapping force is proportional to the light intensity.

One of the more significant applications of optical tweezers is as a tensiometer. By pulling with the optical tweezers, one can measure the forces associated with certain biomolecular interactions, such as the torsional compliance of bacterial flagella, or the force of single motor molecules like myosin and kinesin. In the later case, the kinesin molecules were attached to micron-sized silica beads with sufficiently sparse surface coverage such that, on average, only one molecule was in contact with a microtubule. Using the silica bead as a handle to pull with the optical tweezers, the force exerted by a single kinesin molecule was observed.

Examples of the devices used in this art and of other relevant work are shown in the following references:

U.S. Pat. No. 4,893,886 to Ashkin et el, Jan. 16, 1990;

U.S. Pat. No. 5,100,627 to Buican et al, Mar.31, 1992;

Molloy, J. E., Burns, I. E., Sparrow, J. C., Tregear, R. T., "Single-Molecule Mechanics of Heavy Meromyosin and S1 Interacting with Rabbit or Drosophila Actins Using Optical Tweezers," *Biophysical Journal*, Vol, 68, No. 4, 1995, p. 298s;

Nishizawa, T., Miyata, H., Yoshikawa, H., Ishiwata, S., "Mechanical Properties of Single Protein Motor of Muscle Studied by Optical Tweezers," *Biophysical Journal*, Vol. 68, No. 4, 1995, p. 75s;

Kuo, S.C., Ramanathan, K., Sorg, B., "Single Kinesin Molecules Stressed with Optical Tweezers," *Biophysical Journal*, Vol. 68, No. 4, 1995, p. 74s;

Amos, G., Gill, P., "Optical Tweezers," *Measurement Science & Technology*, Vol. 6, No. 2, 1995, p. 248;

Felgner, H., Mueller, O., Schliwa, M., "Calibration of light forces in optical tweezers," *Applied Optics*, Vol. 34, No. 6, 1995, p. 977;

Liang, H., Wright, W. H., Rieder, C. L., Salmon, E. D., "Directed Movement of Chromosome Arms and Fragments in Mitotic Newt Lung Cells Using Optical Scissors and Optical Tweezers," *Experimental Cell Research*, Vol. 213, No. 1, 1994, p. 308.

Wright, W. H., Sonek, G. J., Barns, M. W., "Parametric study of the forces on microspheres held by optical tweezers," *Applied Optics*, Vol. 33, No. 9, 1994, page 1735;

Wright, W. H., Sonek, G., J., Berns, M. W., "Radiation trapping forces on microspheres with optical tweezers." *Applied Physics Letters*, Vol. 63, No. 6, 1993, p. 715;

Kuo, S. C., Sheetz, M. P., "Force of Single Kinesin Molecules Measured with Optical Tweezers," *Science*. Vol. 260, No. 5105, 1993, p. 232;

Block, S. M., "Making light work with optical tweezers," *Nature*, Vol. 360, No. 6403, 1992, p. 493;

Hong, L, Wright, W. H., Wei, H., Berns, M. W., "Micromanipulation of Mitotic Chromosomes in PTKsub 2 Cells Using Laser-Induced Optical Forces ('Optical Tweezers')," *Experimental Cell Research*, Vol. 197, No. 1, 1991, pp. 21–35;

"Atomic fountains; laser tweezers; optical molasses," *IEEE Micro.*, Vol 12, No. 4, 1993, pp. 88–89;

Block, S. M., "15. Optical Tweezes: A New Tool for Biophysics," *Modern Cell Biology*, Vol. 9, 1990, p. 375;

Dai, J., Sheetz, M.P., "Mechanical properties of neuronal growth cone membranes studied by tether formation with laser optical tweezers." *Biophysical Journal*, Vol. 68, No. 3, 1995, p. 988;

Afzal, R. S., Treacy. E. B., "Optical tweezers using a diode laser," *Review of Scientific instruments*, Vol. 63, No. 4, 1993, pp. 2157–2163;

Ashkin, A., "Trapping of atoms by resonance radiation pressure," *Physical Review Letters*, Vol. 40, 1978, pp. 729–32;

Ashkin, A., Dziedzic, J. M., Bjorkholm, J. E., Chu, S., "Observation of a single-beam gradient force optical trap for dielectric particles," *Optics Letters*, Vol. 11, 1986, pp. 288–90;

Ashkin, A., Dziedzic, J. M., Yamane, T., "Optical trapping and manipulation of single cells using infrared laser beams," *Nature, Vol.* 330, 1987, pp. 769–71;

Ashkin, A., Dziedzic, J. M., "Optical trapping and manipulation of viruses and bacteria," *Science*, Vol. 235, 1987, pp. 1517–20;

Block., S. M., Goldstein, L. S. B., Schnapp, B. J., "Bead movement by single kinesin molecules studied with optical tweezers," *Nature*, Vol. 348, 1990, pp. 348–52.

The disclosures of these references am hereby incorporated by reference in their entirety into this specification.

SUMMARY OF THE INVENTION

An object of the invention is to provide an apparatus and method for detecting and quantitating minute quantities of analytes such as nucleic acids, antigens, and antibodies, receptors and lectins.

A further object of the invention is to provide an apparatus and method for detecting and quantitating such minute quantities when they are in very low concentration.

To these and other ends, the present invention includes a method of detecting and quantitating an analyte, including the method for detecting and quantitating a small quantity of an analyte, the method comprising the following steps: providing a laser light source for emitting a beam of laser light; providing first and second bodies, at least one of the first and second bodies being adapted to be manipulated by the beam of laser light; adhering the analyte to the first body; adhering to the second body a reagent that is reactive with the analyte; bringing the first and second bodies into sufficient proximity to cause a reaction between the analyte and the reagent; separating the first and second bodies by use of the beam of laser light; determining a force necessary to carry out the separating step; and determining a quantity of tho analyte from the force determined in the determining stop.

The present invention also includes an apparatus for detecting and quantitating a small quantity of an analyte, the apparatus comprising the following elements: a laser light source for emitting a beam of laser light; first and second bodies, at least one of the first and second bodies being disposed in the path of the beam of laser light and being adapted to be manipulated by the beam of laser light; means for causing the analyte to adhere to the first body; a reagent that is reactive with the analyte, the reagent being adhered to the second body; means for separating the first and second bodies, after the analyte and the reagent have reacted, by use of the beam of laser light; means for measuring the force that the means for separating must exert to separate the first and second bodies; and means for calculating, on the basis of the force, a quantity of the analyte.

In their experiments, the Applicants coated 4.5 micron latex spheres with antigen. Using the latex spheres as handles, it Is possible to pull on the antigen molecules with optical tweezers. The average minimum laser power required to pull the sphere into the trap and break the bonds between the antigen and either non-specific protein or specific antibodies coated on the glass coverslip was measured. The resulting experimental data indicated that more laser power, hence more force, was required to break the specific antigen/antibody bond versus the non-specific binding cases. This was observed over several orders of antigen concentration, even at the level where we were measuring a single antigen/antibody bond. Similarly, this same process could be followed for the interaction of complementary DNA probes on the latex particle and the glass slide.

A sensitive assay has been developed using this technique by initiating a competitive binding situation between the antigen or DNA sequence on the bead and a similar material in the added sample. These components compete for the binding component attached to the glass slide.

Those skilled in the art who have reviewed this specification will readily appreciate that a very sensitive assay for proteins, organic molecules, receptors, and nucleic acid sequences is possible using this technology. It will also be apparent to those skilled in the art that this assay will detect particulate antigens such as bacteria, viruses and cell components. Those skilled in the art will further appreciate that this assay is able to quantitate analytes within an order of magnitude, with more sensitive quantitation achievable upon optimization of the assay for a particular analyte.

This technology should find major application for detection of infectious diseases, through the detection of disease specific antigens, antibodies, or nucleic acid sequences. It should also find application in detection or any other component presently detectable through PCR, DNA probe technology or immunoassay but at the level of only a few molecules.

BRIEF DESCRIPTION OF THE DRAWINGS

The preferred embodiment of the invention will now be described in greater detail with reference to the drawings, in which.

DETAILED DESCRIPTION OF THE PREFERRED EMBODIMENT

Figure 1:
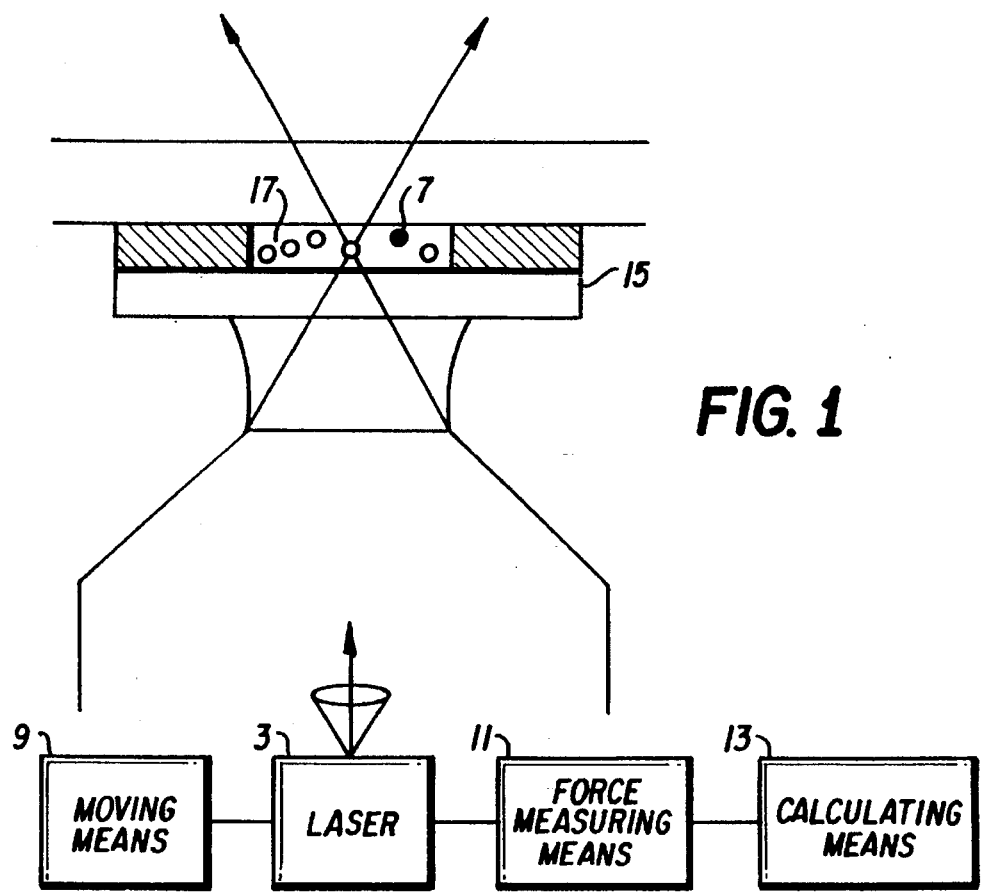
FIG. 1 shows a schematic diagram of an apparatus according to the present invention.

An apparatus according to the present invention is shown in FIG. 1. This figure shows a schematic diagram and is not drawn to scale.

As seen in FIG. 1, the apparatus uses a focused laser beam from a laser light source, such as laser 3 and lens 5 to trap bead 7. The laser should operate within the visible or infrared spectrum. The preferred visible light frequency should be between 375–800 Angstroms. The infrared frequency should be between 800–2500 Angstroms. The size of the bead may be between about 0.5µ about 100µ in diameter. In addition, the bead should comprise a material that does not adsorb the wavelength of the laser beam to prevent the bead from heating during operation of the apparatus. The bead can be moved with the laser under the control of moving means 9. The force needed to move the bead is measured by force measuring means 11. The measured force is outputted to calculating means 13, which uses the measured force to determine the presence and quantity of an analyte, as will be explained in greater detail below.

The bead and second body 15 such as a glass coverslip are exposed to a solution containing the analyte that is placed in well 17. To prevent undesirable heating of the solution, the solution should not absorb the wavelength of the laser beam. To prevent the solution from undesirable heating during operation of the apparatus, the solution should not adsorb the wavelength of the laser beam. The glass cover slip has adhered thereto molecules of reagent (not shown) which react with the analyte. Molecules of the analyte (not shown) are adhered to the bead, preferably with second reagent (not shown). By allowing the analyte to react with the reagent and then measuring the force needed to separate the bead from the glass cover slip, the quantity of the analyte can be determined.

The invention will now be described in further detail with reference to the following illustrative examples.

EXAMPLE #1

PREPARATION OF ANTIBODY COATED CLASS COVERSLIP

A glass coverslip previously boiled in 10% nitric acid and Washed in distilled water was coupled to mouse monoclonal anti-BSA or non-specific antibody through a silane coupling agent previously attached to the glass surface. The coverslip containing immobilized antibody was washed to remove unbound antibody and could be stored under suitable conditions until further use.

To decrease the non-specific attachment of antigen-coated beads to the glass coverslip, the coverslips are preferably prepared using a mixed silane solution comprising 85–99% by volume of an alkylsilane and 1–15% solution of a silane functionalized for coupling of protein. The functionalized silane has a functional group capable of forming a covalent bond with protein, e.g., epoxy, amine, carboxyl, or hydroxy, and may be selected from the group of heterobifunctional cross-linking agents and homobifunctional cross-linking agents. Such agents are well known in the art. This preferred method of preparing the coverslips is described in more detail in Example 1A,

EXAMPLE #1A

PREPARATION OF COVERSLIPS FOR COVALENT COUPLING OF ANTIBODY

Glass coverslips were cleaned by boiling in 10% nitric acid for 1 hour and washed in distilled water until the wash had a neutral pH. Silane solution was prepared by adding 5 ml of 4-glycidoxyropyltrimethoxysilane (GPTMS) and 0.05 to 5 ml of tetramethyl orthosilicate (TMOS) to 100 ml deionized water, The pH of the silane solution was adjusted to pH 4.0 with hydrochloric acid solution. Glass coverslips were dipped into the silane solution and dried at room temperature. They were then heated in a vacuum oven to 110° C. for 90 minutes. The resulting coated coverslips were then used for covalent attachment of the antibody. The decrease in non-specific binding of antigen to the glass coverslips is seen by comparing the data in FIG. 4 with FIG. 2.

EXAMPLE #2

PREPARATION BSA COATED LATEX BEADS

Polystyrene beads (varied between about $0.5\mu$ to about $100\mu$ in diameter), carrying carboxyl groups were coupled to BSA using water soluble carbodiimide, The quantity coupled was decreased in 10-fold steps from $1.49\times10^{-5}$M to a final concentration of $1.49\times10^{-15}$M. These beads were washed to remove uncoupled BSA and stored in 0.05M sodium phosphate buffer, pH 6.6, until used.

EXAMPLE #3

DETECTION OF SINGLE ANTIGEN/ANTIBODY BOND

Figure 3:
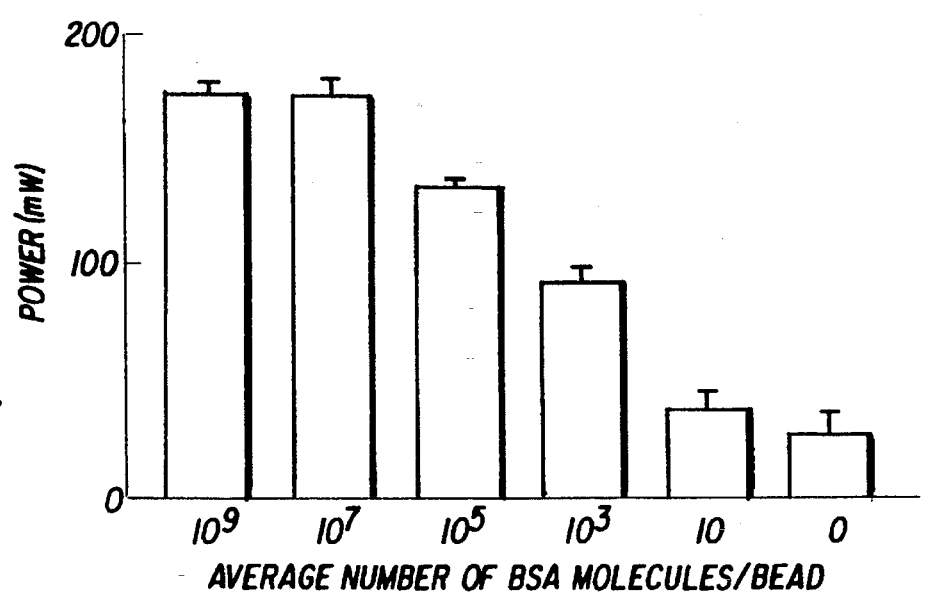
FIG. 3 shows this data recalculated to show the average number of antigen molecules per bead.
Figure 2:
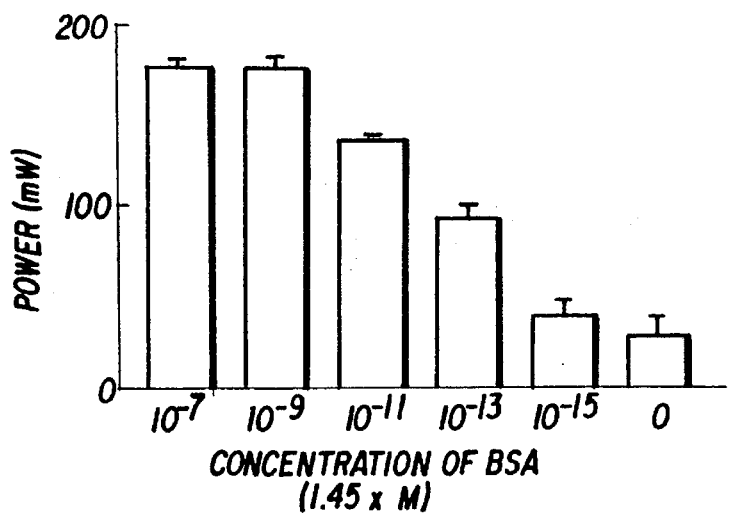
FIG. 2 shows experimental results of Titer Curve for BSA (67,000 MW) coated beads at decreasing concentrations of BSA with constant antibody (Ab) concentration on the glass coverslip in accordance with the present invention.
Figure 4:
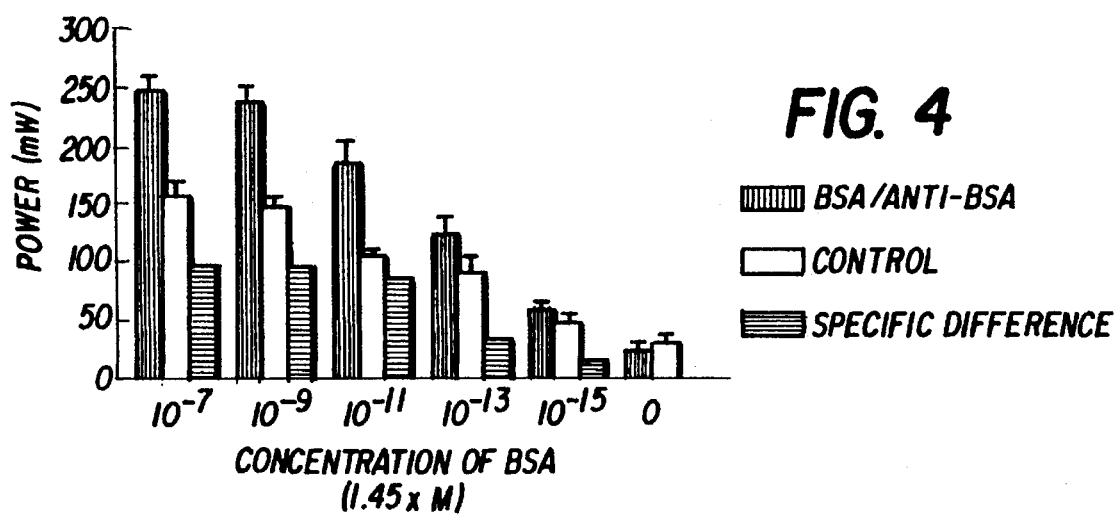
FIG. 4 shows data for a separate binding component using mixed silanes for coupling the antibody to the glass coverslip.

Antigen-coated latex beads (from Example 2) were placed on the antibody-coated coverslip (from Example 1 or 1A) and the force required to optically trap the beads was determined. The antigen/antibody pair was either BSA/anti-BSA to represent a specific binding pair or BSA/nonspecific immunoglobulin as a nonspecific control. At each antigen concentration a minimum of ten beads were tested. The results are shown in FIGS. 2–4, As can be seen in FIG. 4, the average value for the force required to move the BSA-coated bead in the BSA/anti-BSA assay was greater than that required in the nonspecific control assay, Thus, the specific difference between the BSA/anti-BSA and control power values at a given BSA concentration represents the power required to break specific antigen-antibody bonds at that BSA concentration, with the specific difference at the concentration of BSA representing one BSA molecule per bead (compare FIG. 3 and 4) representing the force required to break a single, specific antigen/antibody bond. The ability to detect specific antigen-antibody binding was also tested by comparing BSA/anti-BSA with other nonspecific controls, i.e., BSA/silane, uncoated beads/anti-BSA, and BSA/anti-BSA pretreated with a vast excess of BSA. These assays gave similar results (data not shown).

EXAMPLE #4

DETECTION OF SUB-ZEPTOMOLES OF ANTIGEN

The BSA/Anti-BSA system described in Example 3 was operated in the presence of decreasing concentrations of BSA in solution using 1 microliter samples added to a 100 µl of buffer in a well. Using a concentration of 1 molecule of BSA/1 microliter of sample, the system could detect $1.6\times10^{-18}$ is Molar BSA by competitive binding. This approach will be applicable to any antigen-antibody system regardless of the nature of the antigen. Using BSA coated particles having different BSA concentrations yielded different sensitivities as shown by the displacement bar graphs in FIG. 5.

EXAMPLE #4A

DETECTION OF ANTIGEN IN SERUM

Figure 5:
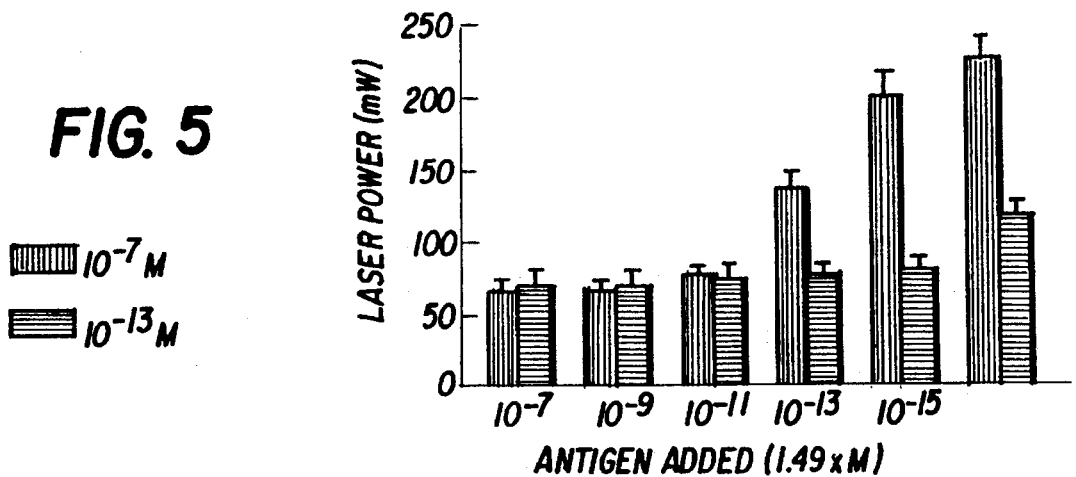
FIG. 5 is a graph showing competitive binding of soluble antigen vs, immobilized antibody/antigen bead at two concentrations of antigen immobilized on the beads.

Human serum was chosen as the diluent for this set of experiments. The antibodies used for the study were the same monoclonal antibodies used in the other examples. Known quantities of BSA were diluted into serum as follows: BSA in a volume of 1 ∥l was added to 100 ∥l of human serum to a final selected concentration. The assay was carried out as described in previous examples except that the serum sample was substituted for BSA diluted in buffer as used in Example #4. The results of these experiments are presented in the table. The standard curve was derived from replotting the bar graphs (FIG. 5). The BSA-coated beads containing $1.49\times10^{-7}$ moles/L of BSA were used unless otherwise noted.

| Sample # | Theoretical Value (moles/L) | Calculated value from Std. Curve |
|---|---|---|
| 1 | $1.49 \times 10^{-10}$ | $1.25 \times 10^{-10}$ |
| 2 | $1.49 \times 10^{-10}$ | $1.62 \times 10^{-10}$ |
| 3 | $1.49 \times 10^{-10}$ | $1.52 \times 10^{-10}$ |
| 4 | $1.49 \times 10^{-13}$ | $1.65 \times 10^{-13}$ |
| 5 | $1.49 \times 10^{-13}$ | $1.80 \times 10^{-13}$ |
| 6 | $1.49 \times 10^{-13}$ | $2.00 \times 10^{-13}$ |
| 7 | $1.49 \times 10^{-15}$ | $1.58 \times 10^{-15}$* |
| 8 | $1.49 \times 10^{-15}$ | $1.42 \times 10^{-15}$* |
| 9 | $1.49 \times 10^{-15}$ | $1.45 \times 10^{-15}$* |

*Assay performed with beads coated at level of $1.49 \times 10^{-13}$ moles/L of BSA.

This data indicates that it is possible to assay a serum sample containing specific antigen and detect and quantitate the analyte therein. It is also obvious to anyone expert in the state-of-art, that one can substitute antibody for antigen in a similar assay with similar results. In this case, the added antibody would compete with the immobilized antibody for the available antigen attached to the beads.

EXAMPLE #4

DETECTION OF DNA SEQUENCES BY DIRECT COMPETITION

A first oligomer of 40 bases containing a terminal amine was covalently coupled to a silanized glass coverslip as described for anti-BSA in Example 1A, A second oligomer also containing a terminal amine and having a sequence complementary to that of the first oligomer was coupled to latex beads as in Example 2 at a concentration previously determined to permit the formation of only one hybrid molecule of the complementary oligomers. The force necessary to separate this hybrid was experimentally determined. Detection of a competing oligomer was accomplished by adding to the system a solution of a single stranded oligomer having a sequence complementary to the sequence of either the oligomer immobilized on the coverslip or fire oligomer on the latex bead at a concentration of 1–1000 molecule/microliter. This added oligomer hybridized with its complementary oligomer immobilized on the coverslip or the head, thereby blocking the binding of the competing oligomer immobilized on the latex bead or coverslip, respectively.

EXAMPLE #6

DETECTION OF LARGE PIECES OF DNA using two single-stranded DNA oligomers having different, noncomplementary sequences, with one oligomer attached to the glass slide and the other oligomer attached to the bead, we were able to detect a unique sequence in a large piece of single-stranded DNA in solution containing both sequences in different locations on the strand. The strand was able to bind to the oligomer on the coverslip and to the oligomer on the bead, thus being caught between the two. The force required to break these bonds exceeded the background, Quantifying the amount of single-stranded DNA in solution can be accomplished with a competitive binding assay using a DNA oligomer having a sequence complementary to the sequence of either the oligomer on the coverslip or the oligomer on the bead to compete with the binding of the DNA strand to the oligomer immobilized on the bead or coverslip, respectively. Detection of 1–100 DNA copies can be performed in this fashion. Therefore, as readily apparent to those skilled in the art, the apparatus of the present invention can be used to detect and quantitate nucleic acid molecules having a known sequence.

The above examples are intended to be illustrative rather than limiting. Those skilled in the art who have reviewed this specification will readily appreciate that the techniques described herein can be adapted to detection and quantitation of other analytes without departing from the scope of the present invention. It will be readily apparent to those skilled in the art that by use of these techniques, it is possible to detect and quantitate any and all nucleic acid sequences, antigens, antibodies and other analytes at extremely low concentrations, i.e. as low as about 1 molecule of analyte per microliter of sample. Detection of analytes present at concentrations less than 1 molecule per microliter can be accomplished with the apparatus of the present invention by allowing sufficient time for the specific binding reaction to occur or by including means of moving the ligand into contact with its corresponding ligand binder. It will also be readily apparent that the ligand and the ligand binder can be on separate beads and that ligands or their corresponding binding agents can be arranged on a "chip" to permit multiple analysis for the desired analyte, e.g, antigen, antibody, DNA target, etc. Thus using mixed beads with different antigens attached or beads of different color, etc., it is possible to run several assays on one sample. This technology provides at rapid, inexpensive, automatable, method for detecting individual molecules of interest to the analytical and clinical chemist. It is applicable for detecting low concentrations of infectious organisms, such as HIV and other viruses, oncogenes, growth factors and other materials where sensitivity is a problem. It can be a major competitor of polymerase chain reaction (PCR), ligase chain reaction (LCR), Q-beta replicase and similar technologies for assays of very low concentrations of nucleic acid material.

We claim:

1. A method of detecting and quantitating an analyte in a sample, the method comprising:
    (a) providing a laser light source for emitting a beam of laser light;
    (b) providing first and second bodies, one of the first and second bodies being adapted to be manipulated by the beam of laser light and the other of the first and second bodies being immovable by the beam of laser light;
    (c) adhering to the first body a first reagent selected from the group consisting of a substance identical to the analyte and analyte competitors;
    (d) adhering to the second body a second reagent capable of binding to both the first reagent and to the analyte, but to only one at a time;
    (e) bringing the first and second bodies into sufficient proximity in the presence of the sample to cause a competition between the first reagent and the analyte in the sample for binding to the second reagent, the competition resulting in a stable complex between the first reagent and the second reagent, the complex holding the first and second bodies together;
    (f) breaking the complex between the first reagent and the second reagent by use of the beam of laser light to separate the first and second bodies;
    (g) determining a force necessary to carry out step (f); and
    (h) determining a quantity of the analyte in the sample from the force determined in step (f).

2. A method as in claim 1, wherein the first body is a bead between about $0.5\mu$ to about $100\mu$ in diameter and comprises a material that does not adsorb light at the wavelength of the beam of laser light.

3. A method as in claim 2, wherein the second body is selected from the group consisting of a glass coverslip and glass slide.

4. A method as in claim 3, wherein the second body is coated with a silane coupling agent for forming a covalent bond with the second reagent.

5. A method as in claim 1, wherein:
    the analyte is an antigen; and
    the second reagent is an antibody capable of binding specifically to the antigen.

6. A method as in claim 1, wherein the analyte and the second reagent comprise nucleic acids having sequences that are complementary to each other.

7. A method as in claim 1, wherein the step of adhering the first reagent to the first body comprises:
    (i) adhering a third reagent to the first body, the third reagent being reactive with the first reagent; and
    (ii) exposing the first body containing the adhered third reagent to the first reagent to cause the adhered third reagent to react with the first reagent.

8. A method as in claim 7, wherein the third reagent comprises a carboxyl group.

9. A method as in claim 7, wherein:
the third reagent and the second reagent both comprise nucleic acids having sequences that are not complementary to each other; and
the analyte comprises a nucleic acid having a sequence with portions that are complementary to the sequences of the third reagent and the second reagent, respectively.

10. A method as in claim 4, wherein the silane coupling agent comprises a mixture of an alkylsilane and a silane functionalized for forming a covalent bond with protein, the functionalized silane being selected from the group consisting of heterobifunctional cross-linking agents and homobifunctional cross-linking agents.

* * * * *

UNITED STATES PATENT AND TRADEMARK OFFICE
CERTIFICATE OF CORRECTION

PATENT NO. : 5,620,857
DATED : April 15, 1997
INVENTOR(S) : Howard H. Weetall; Kristian P. Helmerson; and
Rani B. Kishore It is certified that error appears in the above-indentified patent and that said Letters Patent is hereby corrected as shown below:

On title page, item [75], change "Roni B. Kishore" name to

--Rani B. Kishore--.

Signed and Sealed this

Fifteenth Day of July, 1997

Attest:

BRUCE LEHMAN

*Attesting Officer*  *Commissioner of Patents and Trademarks*